US009132184B2

(12) United States Patent
Vellom et al.

(10) Patent No.: US 9,132,184 B2
(45) Date of Patent: Sep. 15, 2015

(54) STABILIZATION OF VACCINES BY LYOPHILIZATION

(75) Inventors: Daniel C. Vellom, Sudbury, MA (US); James E. Woiszwillo, Watertown, MA (US); Paul DeGeorge, Norwood, MA (US); Peter Ciarametaro, Gloucester, MA (US); Amy Woiszwillo, legal representative, Milford, MA (US); Dara O'Neil, legal representative, Timonium, MD (US); Jennifer Woiszwillo, legal representative, Watertown, MA (US); Cole Woiszwillo, legal representative, Milford, MA (US)

(73) Assignee: Sanofi Pasteur Biologics, LLC, Cambridge, MA (US)

( * ) Notice: Subject to any disclaimer, the term of this patent is extended or adjusted under 35 U.S.C. 154(b) by 717 days.

(21) Appl. No.: 12/513,935

(22) PCT Filed: Nov. 7, 2007

(86) PCT No.: PCT/US2007/023421
§ 371 (c)(1),
(2), (4) Date: Jun. 7, 2010

(87) PCT Pub. No.: WO2008/057550
PCT Pub. Date: May 15, 2008

(65) Prior Publication Data
US 2010/0247573 A1    Sep. 30, 2010

Related U.S. Application Data

(60) Provisional application No. 60/857,424, filed on Nov. 7, 2006.

(51) Int. Cl.
*A61K 39/12* (2006.01)
*C07K 14/005* (2006.01)
*A61K 9/19* (2006.01)
*A61K 39/00* (2006.01)

(52) U.S. Cl.
CPC .............. *A61K 39/12* (2013.01); *C07K 14/005* (2013.01); *A61K 9/19* (2013.01); *A61K 2039/5254* (2013.01); *C12N 2770/24122* (2013.01); *C12N 2770/24134* (2013.01)

(58) Field of Classification Search
CPC ........... C12N 2770/24011; C12N 2770/24034; C12N 2770/24071; C12N 2770/24111; C12N 2770/24134; C12N 2770/24171; A61K 2300/00; A61K 39/12; A61K 9/1623
See application file for complete search history.

(56) References Cited

U.S. PATENT DOCUMENTS

| 4,337,242 | A |   | 6/1982  | Markus et al. |
|-----------|---|---|---------|---------------|
| 4,500,512 | A | * | 2/1985  | Barme .................. 424/218.1 |
| 5,173,418 | A |   | 12/1992 | Molin et al. |
| 5,763,409 | A |   | 6/1998  | Bayol et al. |
| 6,051,238 | A |   | 4/2000  | Volkin et al. |
| 6,184,024 | B1 |  | 2/2001  | Lai et al. |
| 6,210,683 | B1 |  | 4/2001  | Burke et al. |
| 6,284,277 | B1 | * | 9/2001 | Bouloumie et al. .......... 424/489 |
| 6,290,967 | B1 |  | 9/2001  | Volkin et al. |
| 6,497,884 | B1 |  | 12/2002 | Pletnev et al. |
| 6,562,350 | B1 |  | 5/2003  | Wang et al. |
| 6,589,531 | B1 |  | 7/2003  | Andino-Pavlovsky et al. |
| 6,676,936 | B1 |  | 1/2004  | Lai et al. |
| 6,696,281 | B1 |  | 2/2004  | Chambers et al. |
| 6,884,422 | B1 |  | 4/2005  | Liu et al. |
| 6,962,708 | B1 |  | 11/2005 | Chambers et al. |
| 7,094,411 | B2 |  | 8/2006  | Kinney et al. |
| 7,115,270 | B2 |  | 10/2006 | Weltzin et al. |
| 2003/0180329 | A1 | | 9/2003 | Monath et al. |
| 2003/0219475 | A1 | | 11/2003 | Truong-Le |
| 2003/0226155 | A1 | | 12/2003 | Sadeghi et al. |
| 2004/0259224 | A1 | * | 12/2004 | Guirakhoo .................. 435/235.1 |
| 2005/0025782 | A1 | | 2/2005 | Milich et al. |
| 2005/0096288 | A1 | | 5/2005 | Guevara |
| 2005/0255121 | A1 | * | 11/2005 | Campbell et al. .......... 424/184.1 |
| 2006/0008519 | A1 | | 1/2006 | Davidsen et al. |
| 2006/0051844 | A1 | | 3/2006 | Heavner et al. |
| 2006/0121055 | A1 | | 6/2006 | Campbell et al. |
| 2006/0216702 | A1 | | 9/2006 | Compans et al. |

FOREIGN PATENT DOCUMENTS

| EP | 0290197 A2 | 11/1988 |
|----|------------|---------|
| EP | 0353108 A1 | 1/1990 |
| JP | H0853361 A | 2/1996 |
| WO | WO 98/37911 | 9/1998 |
| WO | WO 00/48635 | 8/2000 |
| WO | WO 01/39802 | 6/2001 |
| WO | WO 02/072835 | 9/2002 |
| WO | WO 02/102828 | 12/2002 |
| WO | WO 03/048184 A2 | 6/2003 |
| WO | WO 03/060088 A2 | 7/2003 |
| WO | WO 03/066088 | 8/2003 |
| WO | WO 03/103571 | 12/2003 |
| WO | WO 2004/045529 | 6/2004 |
| WO | WO 2005/055957 | 6/2005 |
| WO | WO 2005/082020 | 9/2005 |
| WO | WO-2005089712 A1 | 9/2005 |
| WO | WO 2006/044857 | 4/2006 |
| WO | WO-2006068307 A1 | 6/2006 |
| WO | WO 2006/116182 | 11/2006 |

OTHER PUBLICATIONS

Steel et al., Virology, 2010, 405:505-512.*

(Continued)

*Primary Examiner* — Stacy B Chen

(74) *Attorney, Agent, or Firm* — Clark & Elbing LLP; Susan M. Michaud

(57) ABSTRACT

This invention provides pharmaceutical compositions, such as vaccines, and methods of making and using such compositions.

20 Claims, 7 Drawing Sheets

(56) References Cited

OTHER PUBLICATIONS

U.S. Appl. No. 09/686,699, filed Nov. 10, 2000, Roy Curtiss III.
International Search Report from International Application No. PCT/US2007/023421, dated Mar. 3, 2008.
Written Opinion from International Application No. PCT/US2007/023421, dated Mar. 3, 2008.
Internnational Preliminary Report on Patentability from International Application No. PCT/US2007/023421, dated May 12, 2009.
Chinese Office Action for Chinese Application No. 200780049359.6, issued Mar. 27, 2012. (English Language Translation Provided).
Eckels et al., "Modification of Dengue Virus Strains by Passage in Primary Dog Kidney Cells: Preparation of Candidate Vaccines and Immunization of Monkeys," Am. J. Trop. Med. Hyg. 69:12-16, 2003.
Supplementary European Search Report from European Patent Application No. 07 86 1777, dated Mar. 26, 2010 (date of completion of search), and Apr. 6, 2010 (date of mailing of report).
Arroyo et al., "ChimeriVax—West Nile Virus Live—Attenuated Vaccine: Preclinical Evaluation of Safety, Immunogenicity, and Efficacy," J. Virol. 78(22):12497-12507, 2004.
Arroyo et al., "Yellow Fever Vector Live-Virus Vaccines: West Nile Virus Vaccine Development," Trends Mol. Med. 7(8):350-354, 2001.
Chambers et al., "Yellow Fever/Japanese Encephalitis Chimeric Viruses: Construction and Biological Properties," J. Virol. 73(4):3095-3101, 1999.
dos Santos et al., "Complete Nucleotide Sequence of Yellow Fever Virus Vaccine Strains 17DD and 17D-213," Virus Res. 35(1):35-41, 1995.
Freestone, "Yellow Fever Vaccine," In Vaccines, S. A. Plotkin and E. A. Mortimer, Jr. (Eds.), W. B. Saunders, Philadelphia, pp. 741-779, 1995.
Galler et al., "Genetic Variability Among Yellow Fever Virus 17D Substrains," Vaccine 16(9-10):1024-1028, 1998.
Guirakhoo et al., "A Single Amino Acid Substitution in the Envelope Protein of Chimeric Yellow Fever—Dengue 1 Vaccine Virus Reduces Neurovirulence for Suckling Mice and Viremia/Viscerotropism for Monkeys," J. Virol. 78(18):9998-10008, 2004.
Guirakhoo et al., "Immunogenicity, Genetic Stability, and Protective Efficacy of a Recombinant, Chimeric Yellow Fever-Japanese Encephalitis Virus (ChimeriVax-JE) as a Live, Attenuated Vaccine Candidate against Japanese Encephalitis," Virology 257(2):363-372, 1999.
Guirakhoo et al., "Recombinant Chimeric Yellow Fever-Dengue Type 2 Virus is Immunogenic and Protective in Nonhuman Primates," J. Virol. 74(12):5477-5485, 2000.
Guirakhoo et al., "Safety and Efficacy of Chimeric Yellow Fever-Dengue Virus Tetravalent Vaccine Formulations in Nonhuman Primates," J. Virol. 78(9):4761-4775, 2004.
Monath et al., "Chimeric Live, Attenuated Vaccine against Japanese Encephalitis (ChimeriVax-JE): Phase 2 Clinical Trials for Safety and Immunogenicity, Effect of Vaccine Dose and Schedule, and Memory Response to Challenge with Inactivated Japanese Encephalitis Antigen," J. Infect. Dis. 188(8):1213-1230, 2003.
Monath, "Molecular Distinctions Between Attenuated (Vaccine) and Virulent Yellow Fever Viruses," In Vaccines, Plotkin and Orenstein (Eds.), $3^{rd}$ edition, Saunders, Philadelphia, pp. 815-879, 1999.
Monath et al., "Recombinant, Chimaeric Live, Attenuated Vaccine (ChimeriVax™) Incorporating the Envelope Genes of Japanese Encephalitis (SA14-14-2) Virus and the Capsid and Nonstructural Genes of Yellow Fever (17D) Virus is Safe, Immunogenic and Protective in Non-human Primates," Vaccine 17(15-16):1869-1882, 1999.
Pugachev et al., "Construction of Yellow Fever/St. Louis Encephalitis Chimeric Virus and the Use of Chimeras as a Diagnostic Tool," Am. J. Trop. Med. Hyg. 71(5):639-645, 2004.
Pugachev et al., "Chimeric Vaccines Against Japanese Encephalitis, Dengue, and West Nile," In New Generation Vaccines, $3^{rd}$ Edition, Levine et al. (Eds.), Marcel Dekker, New York, pp. 559, 567, and 568, 2004.
Rice et al., "Nucleotide Sequence of Yellow Fever Virus: Implications for Flavivirus Gene Expression and Evolution," Science 229(4715):726-733, 1985.
Rice et al., "Transcription of Infectious Yellow Fever RNA from Full-length cDNA Templates Produced by In Vitro Ligation," New Biol. 1(3):285-296, 1989.
Smithburn et al., "Yellow Fever Vaccination," World Health Org., Geneva, pp. 1-238, 1956.
Notice of Reasons for Rejection issued in Japanese Patent Application No. 2009-535362, dispatched Nov. 28, 2012 (English Language Translation Provided) (7 pages).
Notice of Reasons for Rejection for Japanese Patent Application No. 2009-535362, dated Nov. 25, 2013 (7 pages). English language translation provided.

\* cited by examiner

Figure 1: JEPD-018 Titer Loss from 37°C Storage
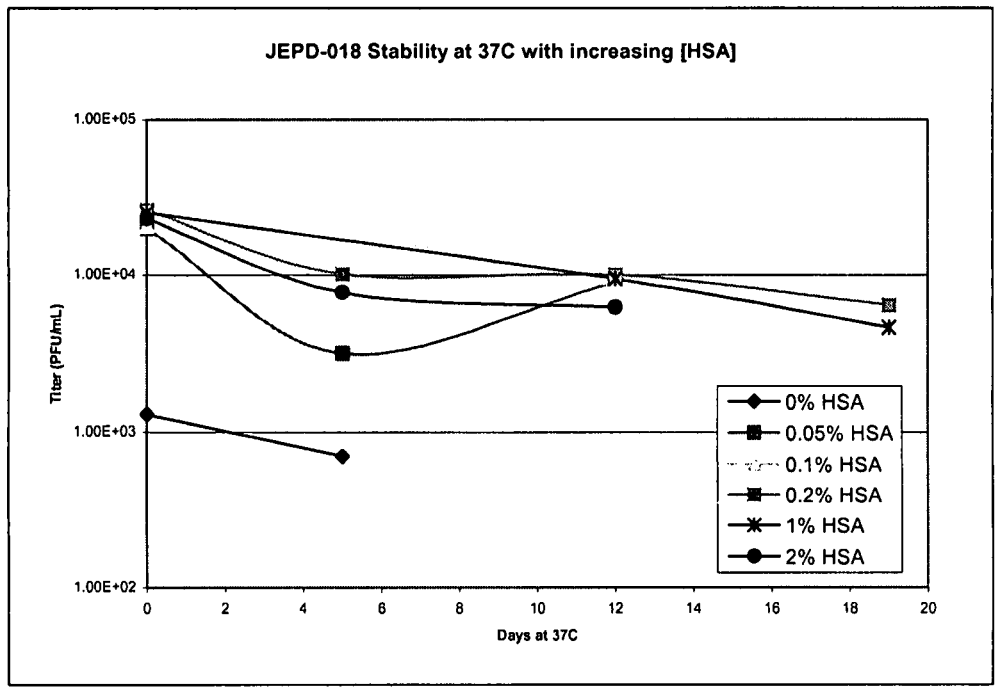
Figure 2: WNPD-033 Titer Loss from 37°C Storage with and without Histidine
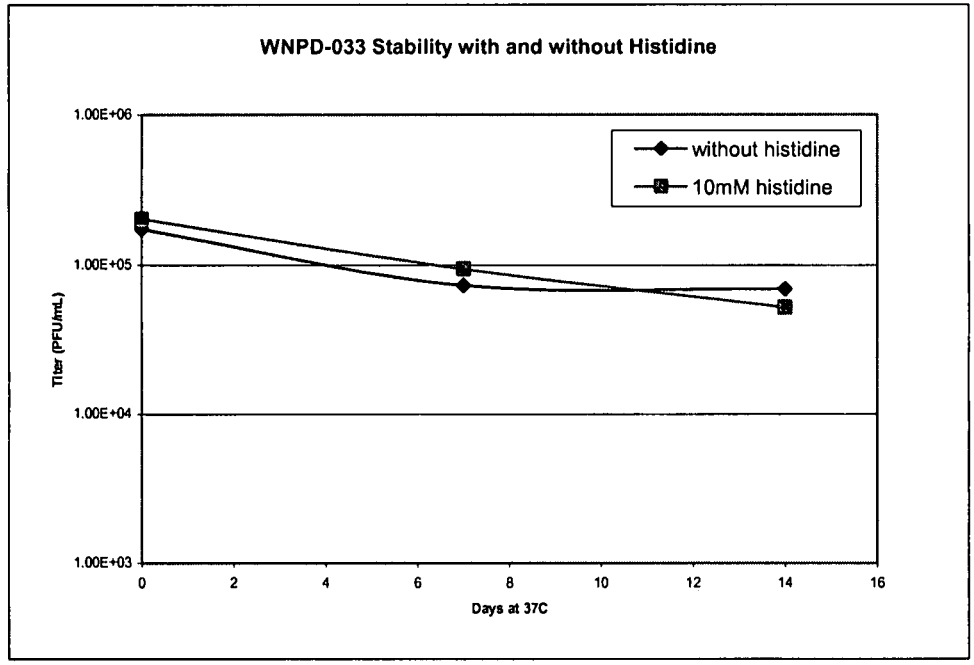

Figure 3: WNPD-045 Titer Loss from 37°C Storage with and without Potassium Glutamate
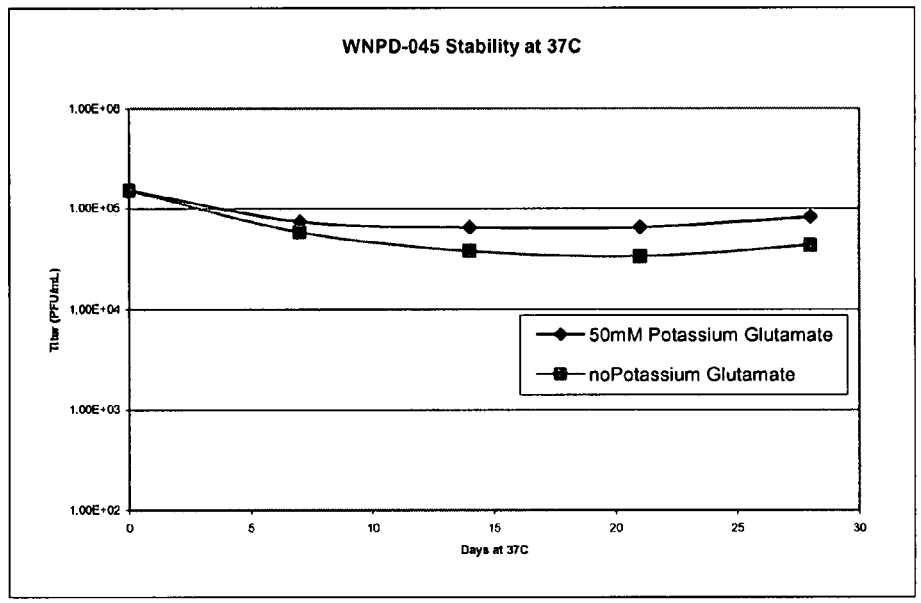
Figure 4: JEPD-145 Titer Loss from 37°C Storage with different [lactose]
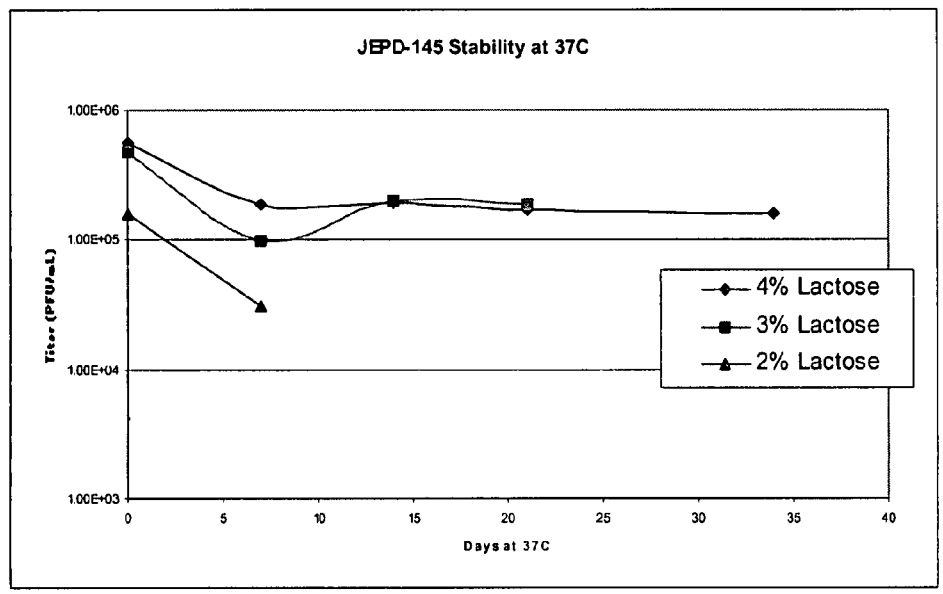

Figure 5: Titer Loss from 37°C Storage in Single Sugar Formulations
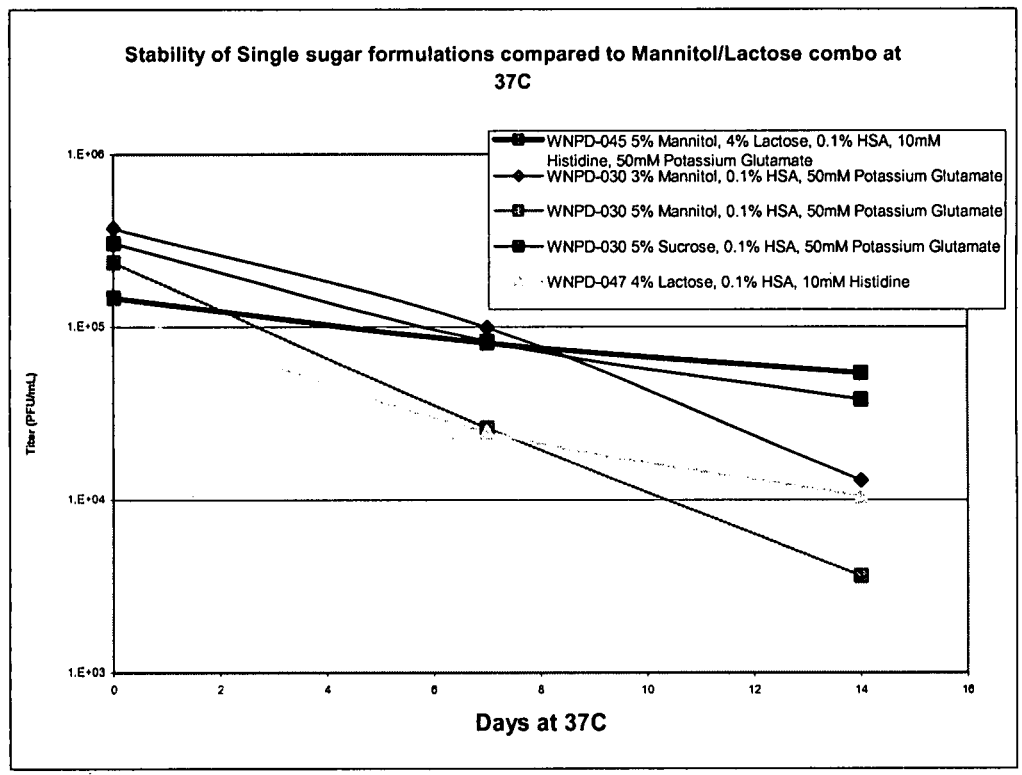
Figure 6: Titer Loss from 37°C Storage in Annealed Samples
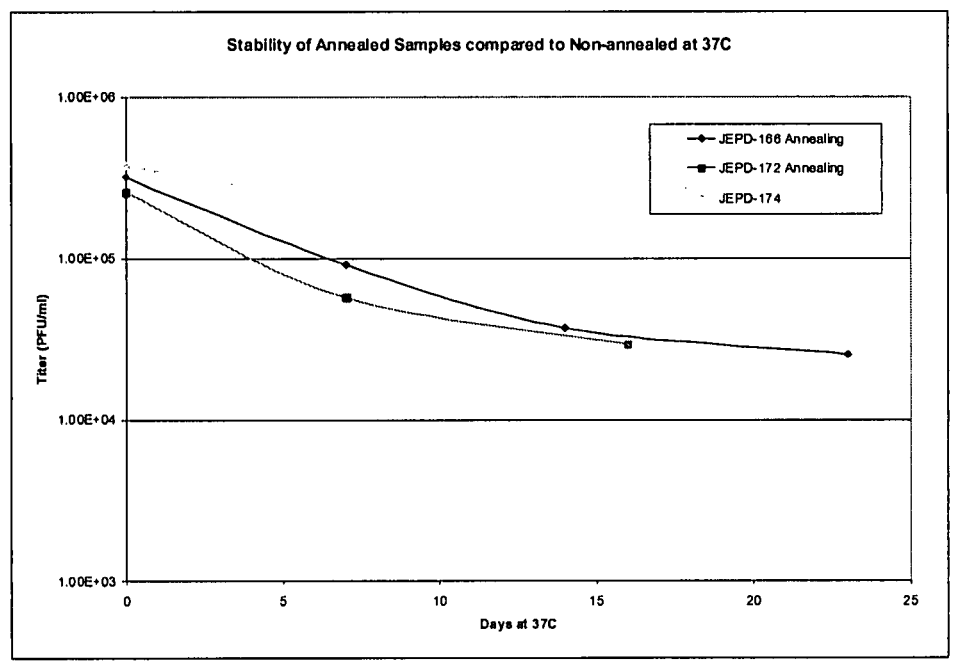

Figure 7: DSC Thermalgram for a 4% Lactose formulation
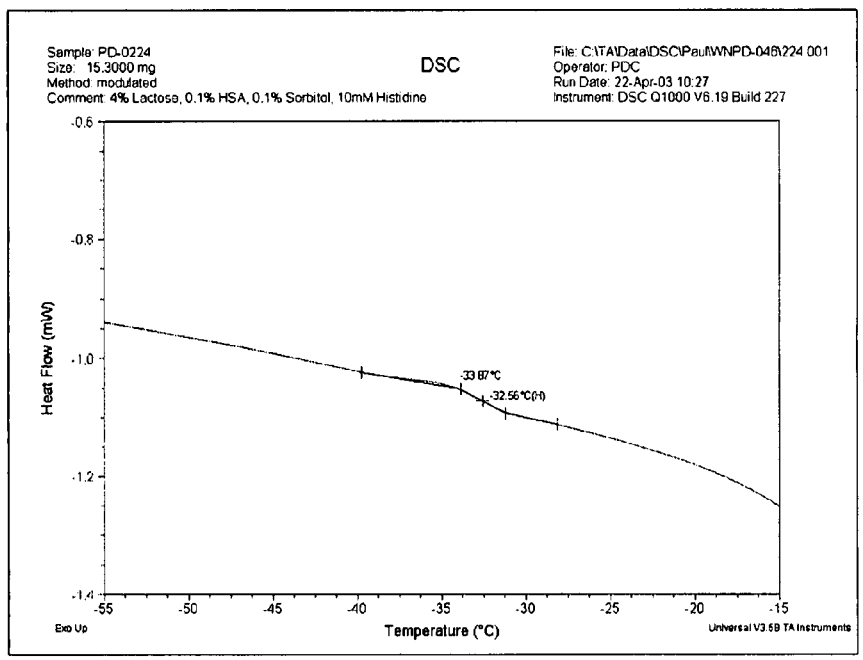
Figure 8: DSC Thermalgram for Annealing of a 5% Mannitol, 4% Lactose formulation
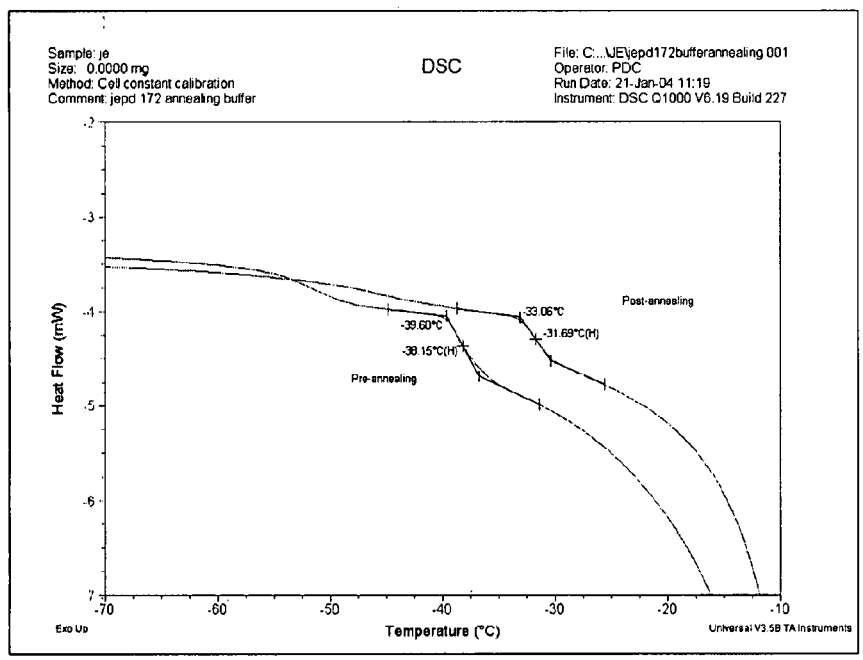

Figure 9: Real-time Stability of Final Formulation at −80°C
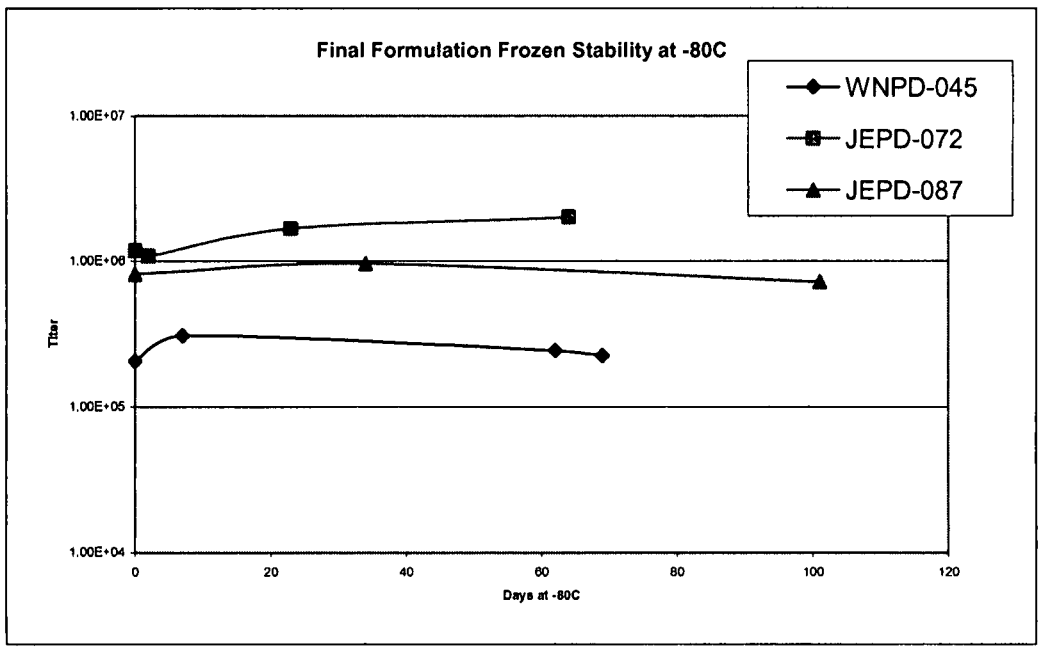
Figure 10: DSC Themalgram (modulated) of Final Formulation
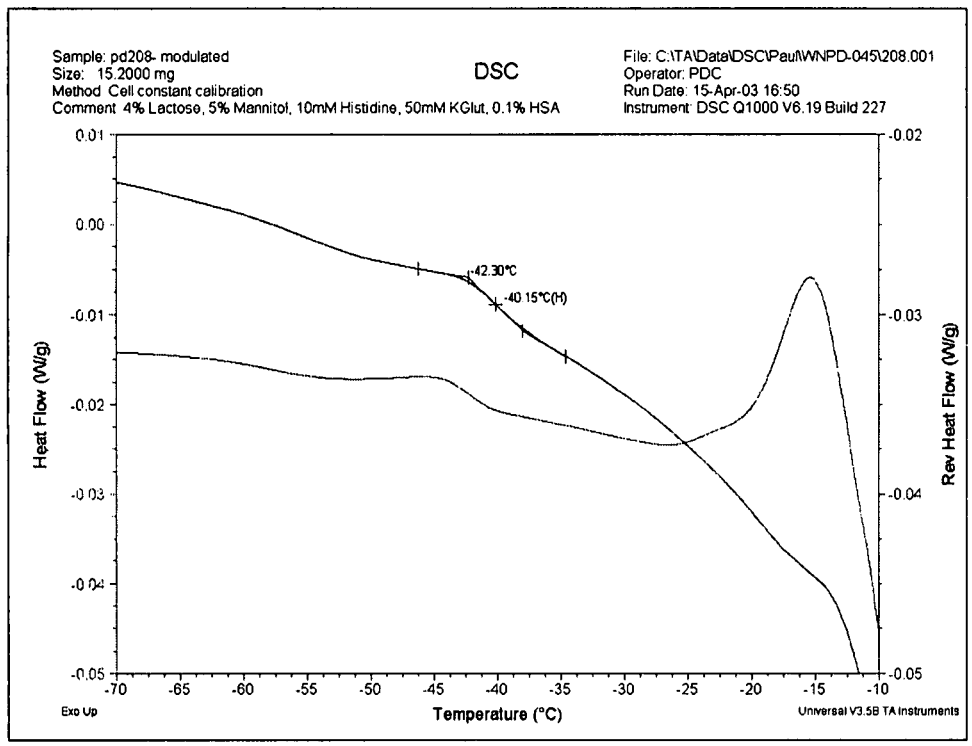

Figure 11: DSC Thermalgram of Final Formulation

Figure 12: Correlation of Stability to Residual Moisture of Lyophilized ChimeriVax (Experiments JEPD-072, JEPD-087, JEPD-145, JEPD-147, JEPD-151)

Figure 13: JEPD-151 Lyophilization Data
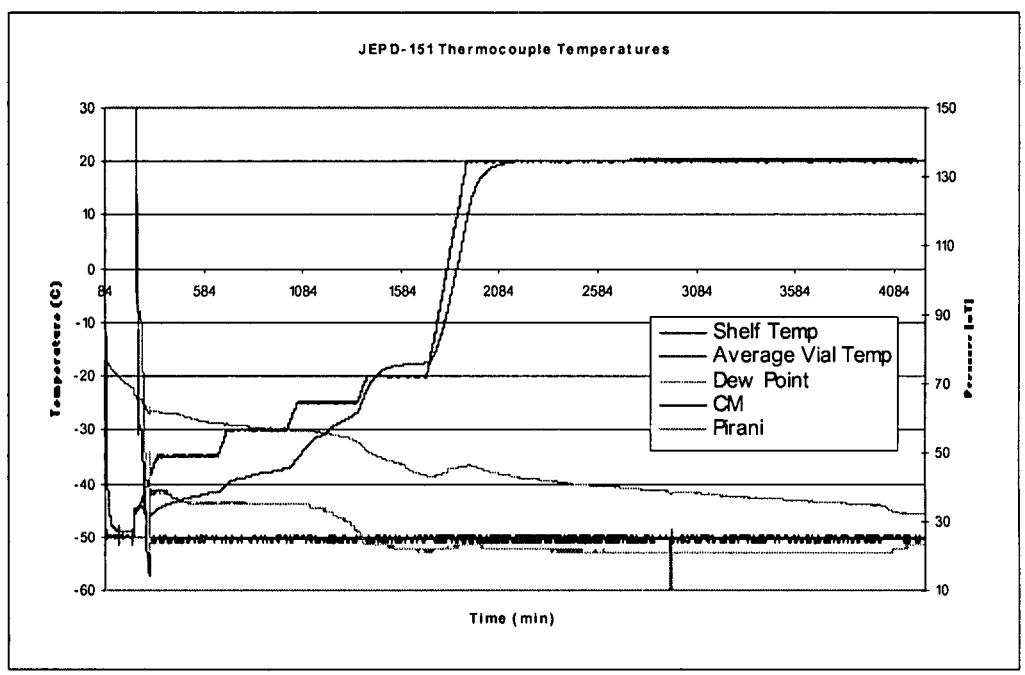

STABILIZATION OF VACCINES BY LYOPHILIZATION

CROSS-REFERENCE TO RELATED APPLICATIONS

This application claims priority under 35 U.S.C. §371 from international application PCT/US2007/023421, filed Nov. 7, 2007, which claims priority from U.S. Provisional Application 60/857,424, filed Nov. 7, 2006.

FIELD OF THE INVENTION

This invention relates to pharmaceutical compositions, such as vaccines, and methods of making and using such compositions.

BACKGROUND OF THE INVENTION

Vaccination is one of the greatest achievements of medicine, and has spared millions of people the effects of devastating diseases. Before vaccines became widely used, infectious diseases killed thousands of children and adults each year in the United States alone, and so many more worldwide. Vaccination is widely used to prevent and treat infection by bacteria, viruses, and other pathogens, and also is an approach that is used in the prevention and treatment of cancer. Several different approaches are used in vaccination, including the administration of killed pathogen, live-attenuated pathogen, and inactive pathogen subunits. In the case of viral infection, live vaccines have been found to confer the most potent and durable protective immune responses.

Live-attenuated vaccines have been developed against *flaviviruses*, which are small, enveloped, positive-strand RNA viruses that are generally transmitted by infected mosquitoes and ticks. The *Flavivirus* genus of the Flaviviridae family includes approximately 70 viruses, many of which, such as yellow fever (YF), dengue (DEN), Japanese encephalitis (JE), and tick-borne encephalitis (TBE) viruses, are major human pathogens (rev. in Burke and Monath, Fields Virology, 4$^{th}$ Ed., 1043-1126, 2001).

Different approaches have been used in the development of vaccines against *flaviviruses*. In the case of yellow fever virus, for example, two vaccines (yellow fever 17D and the French neurotropic vaccine) have been developed by serial passage (Monath, "Yellow Fever," In Plotkin and Orenstein, Vaccines, 3$^{rd}$ ed., Saunders, Philadelphia, pp. 815-879, 1999). Another approach to attenuation of *flaviviruses* for use in vaccination involves the construction of chimeric *flaviviruses*, which include components of two (or more) different *flaviviruses*. Understanding how such chimeras are constructed requires an explanation of the structure of the flavivirus genome.

*Flavivirus* proteins are produced by translation of a single, long open reading frame to generate a polyprotein, which is followed by a complex series of post-translational proteolytic cleavages of the polyprotein by a combination of host and viral proteases to generate mature viral proteins (Amberg et al., J. Virol. 73:8083-8094, 1999; Rice, "Flaviviridae," In *Virology*, Fields (ed.), Raven-Lippincott, New York, 1995, Volume I, p. 937). The virus structural proteins are arranged in the polyprotein in the order C-prM-E, where "C" is capsid, "prM" is a precursor of the viral envelope-bound M protein, and "E" is the envelope protein. These proteins are present in the N-terminal region of the polyprotein, while the non-structural proteins (NS1, NS2A, NS2B, NS3, NS4A, NS4B, and NS5) are located in the C-terminal region of the polyprotein.

Chimeric *flaviviruses* have been made that include structural and non-structural proteins from different *flaviviruses*. For example, the so-called ChimeriVax™ technology employs the yellow fever 17D virus capsid and nonstructural proteins to deliver the envelope proteins (prM and E) of other *flaviviruses* (see, e.g., Chambers et al., J. Virol. 73:3095-3101, 1999). This technology has been used to develop vaccine candidates against dengue, Japanese encephalitis (JE), West Nile (WN), and St. Louis encephalitis (SLE) viruses (see, e.g., Pugachev et al., in New Generation Vaccines, 3$^{rd}$ ed., Levine et al., eds., Marcel Dekker, New York, Basel, pp. 559-571, 2004; Chambers et al., J. Virol. 73:3095-3101, 1999; Guirakhoo et al., Virology 257:363-372, 1999; Monath et al., Vaccine 17:1869-1882, 1999; Guirakhoo et al., J. Virol. 74:5477-5485, 2000; Arroyo et al., Trends Mol. Med. 7:350-354, 2001; Guirakhoo et al., J. Virol. 78:4761-4775, 2004; Guirakhoo et al., J. Virol. 78:9998-10008, 2004; Monath et al., J. Infect. Dis. 188:1213-1230, 2003; Arroyo et al., J. Virol. 78:12497-12507, 2004; and Pugachev et al., Am. J. Trop. Med. Hyg. 71:639-645, 2004).

Central to the successful use and commercialization of vaccines is the manner by which they are processed and formulated, to ensure stability and maintenance of efficacy under conditions in which the vaccines are shipped and stored prior to use. Lyophilization is an approach involved in the processing of some vaccine products, and is essentially a freeze-drying process that, under low pressures, removes water through sublimation, and leaves the product as a dried cake with a small amount of moisture. This process can be advantageous to vaccines, including chimeric *flavivirus* vaccines as described above, because such vaccines tend to be more stable in a low moisture environment. Lyophilization can also increase the storage temperature of the product and make it easier to transport. A critical factor impacting the efficacy of the lyophilization process is the formulation of the vaccine. For example, it is desirable that the formulation, upon removal of water, enhances the stability of the product. Typically, a vaccine formulation will contain any or all of the following components: a bulking agent (e.g., a sugar), a stabilizer (e.g., a sugar or a protein), and a buffer. The development of effective and efficient processing methods and formulations is therefore of great importance to the development of clinically useful and commercially successful vaccines, including *flavivirus* vaccines, as discussed above.

SUMMARY OF THE INVENTION

The invention provides compositions including one or more live, attenuated *flavivirus* vaccines, one or more stabilizers, one or more bulking agents, and one or more buffer components. In one example, the stabilizer is human serum albumin (HSA) (e.g., non-recombinant human serum albumin (HSA) or recombinant human serum albumin (rHA)) (e.g., about 0.05-2.0% or 0.1%). Examples of bulking agents that can be included in the compositions of the invention are lactose (e.g., about 2-10% or 4%) and/or mannitol (e.g., about 2-10% or 5%), while examples of buffer components that can be included in the compositions are histidine (e.g., about 1-20 mM or 10 mM) and/or potassium glutamate (e.g., about 20-80 mM or 50 mM). The compositions can be in freeze-dried form or in liquid form, prior to freeze-drying. Further, the pH of the compositions can be, e.g., 6-10, 7-9, 7.5-8.5, or 7.9-8.1.

The live, attenuated *flavivirus* vaccines included in the compositions of the invention can be, for example, chimeric *flaviviruses*, such as chimeric *flaviviruses* that include structural proteins of a first *flavivirus* and non-structural proteins of a second, different *flavivirus*. In an example, such a chimeric *flavivirus* includes pre-membrane/membrane and envelope proteins of the first *flavivirus* and capsid and nonstructural proteins of the second, different *flavivirus*.

The first and second *flaviviruses* can be, independently, selected from the group consisting of yellow fever (e.g., YF17D), Japanese encephalitis, dengue-1, dengue-2, dengue-3, dengue-4, Murray Valley encephalitis, St. Louis encephalitis, West Nile, Kunjin, Rocio encephalitis, Ilheus, Central European encephalitis, Siberian encephalitis, Russian Spring-Summer encephalitis, Kyasanur Forest Disease, Alkhurma, Omsk Hemorrhagic fever, Louping ill, Powassan, Negishi, Absettarov, Hansalova, Apoi, and Hypr viruses. In specific examples, the first *flavivirus* is a Japanese encephalitis virus or a West Nile virus, and the second *flavivirus* is a yellow fever virus (e.g., YF17D).

Also included in the invention are compositions including one or more proteins and/or virus-based pharmaceutical products, human serum albumin (e.g., non-recombinant human serum albumin (HSA) or recombinant human serum albumin (rHA)) (e.g., about 0.05-2.0% or 0.1%), glutamic acid alkali metal salt(s) (e.g., potassium glutamate) (e.g., about 20-80 mM or 50 mM), one or more additional amino acids (e.g., histidine) (e.g., about 1-20 mM or 10 mM), and one or more sugars or sugar alcohols (e.g., lactose and/or mannitol) (e.g., about 2-10%, 4%, or 5%). The compositions can be in freeze-dried form or in liquid form, prior to freeze-drying. Further, the pH of the compositions can be, e.g., 6-10, 7-9, 7.5-8.5, or 7.9-8.1.

In one example, the virus-based pharmaceutical product includes a smallpox vaccine (e.g., a vaccinia virus or an attenuated vaccinia virus, such as, for example, ACAM1000, ACAM2000, or Modified Vaccinia Ankara (MVA)). In another example, the protein-based pharmaceutical product comprises a Hepatitis B virus core protein fusion (e.g., a Hepatitis B virus core protein fusion further including one or more influenza M2e peptides). Further, in another example, the protein-based pharmaceutical product includes a toxin or toxoid of *Clostridium difficile*.

Also included in the invention are methods of preparing therapeutic compositions, which involve subjecting a composition such as those described above to a freeze-drying process. This process can involve the steps of freezing, primary drying, and secondary drying. In an example, the freezing step involves freezing at about −50° C. for about 120 minutes. The primary drying step can involve ramp steps including ramping at about +0.1° C./minute to a shelf temperature of about −40° C., holding for about 500 minutes; ramping at about +0.1° C./minute to a shelf temperature of about −35° C., holding for about 500 minutes; ramping at about +0.1° C./minute to a shelf temperature of about −30° C., holding for about 500 minutes, and ramping at about +0.1° C./minute to a shelf temperature of about −25° C., holding for about 800 minutes. In this example, the secondary drying step can involve ramp steps including ramping at about +0.1° C./minute to a shelf temperature of about +20° C., holding for about 800 minutes.

In another example, the freezing step can involve freezing at about −40° C. for about 60 minutes. The primary drying step can involve ramp steps including ramping at about +0.5° C./minute to a shelf temperature of about −5° C., holding for about 300 minutes; and ramping at about −0.5° C./minute to a shelf temperature of about −0° C., holding for about 300 minutes. The secondary drying step can involve ramp steps including ramping at about +0.2° C./minute to a shelf temperature of about +30° C., holding for about 600 minutes; and ramping at about −1.0° C./minute to a shelf temperature of about +5° C., holding for about 9999 minutes.

The invention also includes methods of preventing or treating one or more diseases or conditions in a subject, which involve administration of one or more compositions of the invention, as described above and elsewhere herein. In certain examples of these methods, the subject is at risk of developing or has a *flavivirus* (e.g., Japanese encephalitis virus, West Nile virus, dengue virus, or yellow fever virus infection), smallpox, influenza, or *Clostridium difficile*. Further, the invention includes use of the compositions and preparations described herein in the prevention and treatment of diseases and conditions as described herein, as well as for the preparation of medicaments for use in these purposes. In general, the methods are carried out to "prevent" a disease, condition, or infection of a subject if the subject does not have the disease, condition, or infection prior to administration of the material or composition of the invention. The methods are carried out to "treat" a disease, condition, or infection of a subject if the subject has such a disease, condition, or infection. The prevention and/or treatment can be done to reduce the effects that would otherwise be obtained in the absence of administration, or to eliminate such effects.

The invention provides several advantages. For example, as discussed above, it is critical to the effective use of pharmaceutical compositions including protein and/or virus components, such as vaccines, that the compositions remain stable under varying conditions of shipment and storage. As is discussed further below, the present invention provides formulations and processing steps that result in the preparation of compositions with enhanced stability. Other features and advantages of the invention will be apparent from the following detailed description, the drawings, and the claims.

BRIEF DESCRIPTION OF THE DRAWINGS

FIG. 1 is a graph showing titer loss from 37° C. storage in experiment JEPD-018.

FIG. 2 is a graph showing stability with and without histidine in experiment WNPD-033.

FIG. 3 is a graph showing stability with and without potassium glutamate at 37° C. in experiment WNPD-045.

FIG. 4 is a graph showing stability with different concentrations of lactose at 37° C. in experiment JEPD-145.

FIG. 5 is a graph showing the stability of single sugar formulations as compared to a mannitol/lactose combination at 37° C.

FIG. 6 is a graph showing titer loss from 37° C. storage in annealed samples.

FIG. 7 is a thermalgram of a 4% lactose solution, which has a glass transition of −32.6° C.

FIG. 8 is a thermalgram showing that, when 5% mannitol is added to a formulation, the glass transition temperature is depressed approximately 6° C. to −38° C.

FIG. 9 is a graph showing real-time stability of a final formulation at −80° C.

FIG. 10 is a thermalgram from a WNPD-045 sample analyzed using modulated DSC to improve resolution.

FIG. 11 is a thermalgram of a sample from JEPD-172 that showed sufficient resolution without using modulated scanning.

FIG. 12 is a graph showing the correlation of stability to residual moisture of lyophilized ChimeriVax™ in the indicated experiments.

FIG. 13 is a graph showing the thermocouple temperatures of experiment JEPD-151.

DETAILED DESCRIPTION

The invention provides compositions and methods that can be used for the preparation of viral and/or protein-based pharmaceutical products, including live viral vaccines, as described further below. The compositions of the invention include components (e.g., particular stabilizers, bulking agents, and buffers) that, as described below, we have found to be advantageous in the preparation of vaccines, while the methods include steps, which involve lyophilization, that also provide advantages. The invention also provides prophylactic and therapeutic methods employing the compositions described herein. The compositions and methods of the invention are described further, as follows.

Compositions of the invention include one or more protein and/or virus-based therapeutic agents, as well as one or more stabilizers, bulking agents, and/or buffer components. A specific example of a composition of the invention is described in further detail below and includes a chimeric *flavivirus* vaccine, human serum albumin (0.1%) as a stabilizer, mannitol (5%) and lactose (4%) as bulking agents, and histidine (10 mM) and potassium glutamate (50 mM) as buffer components. In addition to this specific example, the invention also includes compositions in which components of these types are varied in identity and/or amount, as described as follows.

Stabilizers that can be present in compositions of the invention include serum albumin proteins. A preferred serum albumin protein is human serum albumin (HSA), whether in non-recombinant or recombinant form. An additional example of a serum albumin protein that can be included in the compositions invention is bovine serum albumin. In addition to serum albumins, other stabilizers that can be included in the compositions of the invention are gelatins, such as human gelatin (e.g., a recombinant human gelatin, which may be wild-type or engineered) and porcine gelatin, casein, PVP, and combinations of any of stabilizers mentioned herein (or others known in the art). In the case of human serum albumin, the amount of this component can be, e.g., about 0.05-2.0%, 0.075-1.0%, or 0.1%.

Bulking agents that can be present in the compositions of the invention include sugars, such as lactose, sucrose, and fructose, and/or sugar alcohols, such as mannitol and sorbitol. As is discussed further below, in compositions of the invention including mannitol, it may be preferable for this component to be in an amorphous rather than crystalline form. Further, in certain examples, it may be preferable for the compositions of the invention to include combinations of sugars and/or sugar alcohols. In one example, which is described further below, compositions of the invention can include a combination of lactose and mannitol, with the latter preferably being in amorphous form. In one example, lactose is present at about 1-10%, 2-8%, or 4-6% (e.g., 4%), while mannitol is present at about 1-10%, 2-8%, or 4-6% (e.g., 5%).

As is noted above, in addition to stabilizers and bulking agents, the compositions of the invention can include buffer components, such as amino acids, which may serve to contribute to the maintenance of, e.g., a particular pH level or range, and/or product stability. One example of a buffer component that can be included in the compositions of the invention is histidine, which may be present in the compositions in a concentration of about, e.g., 1-20, 5-15, or 10 mM. Another example of a buffer component is glutamic acid alkali metal salts, such as sodium or potassium glutamate, which may be present in the compositions in a concentration of about 10-100, 25-75, or 50 mM. Further, the compositions are generally of a pH of, e.g., 6-10, 7-9, 7.5-8.5, or 7.9-8.1.

The compositions of the invention also include one or more active, therapeutic components, which can be peptide or protein-based therapeutic agents, as well as viruses, such as live, attenuated virus vaccines. One example of a type of the latter group of therapeutic agents (live, attenuated virus vaccines) is *flavivirus* vaccines, such as yellow fever virus vaccines. A specific example of such a yellow fever virus vaccine is the YF17D vaccine strain (Smithburn et al., "Yellow Fever Vaccination," World Health Org., p. 238, 1956; Freestone, in Plotkin et al. (eds.), Vaccines, $2^{nd}$ edition, W. B. Saunders, Philadelphia, 1995). Other yellow fever virus strains, e.g., YF17DD (GenBank Accession No. U 17066) and YF 17D-213 (GenBank Accession No. U17067) (dos Santos et al., Virus Res. 35:35-41, 1995), YF17D-204 France (X15067, X15062), YF17D-204, 234 US (Rice et al., Science 229:726-733, 1985; Rice et al., New Biologist 1:285-296, 1989; C 03700, K 02749), and yellow fever virus strains described by Galler et al., Vaccine 16 (9/10):1024-1028, 1998, can also be present in the compositions of the invention.

Additional *flaviviruses* that can be present in the compositions of the invention include other mosquito-borne *flaviviruses*, such as Japanese encephalitis (e.g., SA14-14-2), dengue (serotypes 1-4), Murray Valley encephalitis, St. Louis encephalitis, West Nile, Kunjin, Rocio encephalitis, and Ilheus viruses; tick-borne *flaviviruses*, such as Central European encephalitis, Siberian encephalitis, Russian Spring-Summer encephalitis, Kyasanur Forest Disease, Alkhurma, Omsk Hemorrhagic fever, Louping ill, Powassan, Negishi, Absettarov, Hansalova, Apoi, and Hypr viruses; as well as viruses from the Hepacivirus genus (e.g., Hepatitis C virus).

In addition to the viruses listed above, as well as other *flaviviruses*, chimeric *flaviviruses* can also be included in the compositions of the invention. These chimeras can consist of a *flavivirus* (i.e., a backbone *flavivirus*) in which a structural protein (or proteins) has been replaced with a corresponding structural protein (or proteins) of a second virus (i.e., a test or a predetermined virus, such as a *flavivirus*; see, e.g., U.S. Pat. No. 6,696,281; U.S. Pat. No. 6,184,024; U.S. Pat. No. 6,676,936; and U.S. Pat. No. 6,497,884). For example, the chimeras can consist of a backbone *flavivirus* (e.g., a yellow fever virus) in which the membrane and envelope proteins of the *flavivirus* have been replaced with the membrane and envelope of a second, test virus (e.g., West Nile virus, a dengue virus (serotype 1, 2, 3, or 4), Japanese encephalitis virus, or another virus, such as any of those mentioned herein). The chimeric viruses can be made from any combination of viruses, but typically the virus against which immunity is sought is the source of the inserted structural protein(s).

A specific example of a type of chimeric virus that can be included in the compositions of the invention is the yellow fever human vaccine strain, YF17D, in which the membrane protein and the envelope protein have been replaced with the membrane protein and the envelope protein of another *flavivirus*, such as a West Nile virus, dengue virus (serotype 1, 2, 3, or 4), Japanese encephalitis virus, St. Louis encephalitis virus, Murray Valley encephalitis virus, or any other *flavivirus*, such as one of those listed above. Chimeric *flaviviruses* made using this approach have been designated as so-called "ChimeriVax" viruses. The following chimeric *flaviviruses*, which were made using the ChimeriVax™ technology and deposited with the American Type Culture Collection (ATCC) in Manassas, Va., U.S.A. under the terms of the Budapest Treaty and granted a deposit date of Jan. 6, 1998, can be used to make viruses of the invention: Chimeric Yellow Fever 17D/Dengue Type 2 Virus (YF/DEN-2; ATCC accession number ATCC VR-2593) and Chimeric Yellow Fever 17D/Japanese Encephalitis SA14-14-2 Virus (YF/JE A1.3; ATCC accession number ATCC VR-2594).

Details of making chimeric viruses that can be used in the invention are provided, for example, in the following publications: WO 98/37911; WO 01/39802; Chambers et al., J. Virol. 73:3095-3101, 1999; WO 03/103571; WO 2004/

045529; U.S. Pat. No. 6,696,281; U.S. Pat. No. 6,184,024; U.S. Pat. No. 6,676,936; and U.S. Pat. No. 6,497,884. Additional specific examples of chimeric *flaviviruses* that can be present in the compositions of the invention, and which may include particular attenuating mutations, are described for example in WO 02/072835, WO 02/102828, WO 03/103571, WO 2004/045529, WO 2005/082020, WO 2006/044857, WO 2006/116182, and U.S. Pat. No. 6,589,531.

Additional virus vaccines that can be present in the compositions of the invention include smallpox vaccines (e.g., vaccines based on vaccinia viruses, including ACAM1000, ACAM2000, Modified Vaccinia Ankara (MVA), and Lister, and vaccines based on monkeypox), and Herpes Viruses and vaccines (e.g., HSV-1 and recombinants thereof and HSV-2 and recombinants thereof) (see, e.g., U.S. Pat. No. 7,115,270).

In addition to viruses, the compositions of the invention can also include therapeutic or vaccine peptides or proteins such as, for example, Hepatitis B core protein fusion constructs (e.g., Hepatitis B core proteins fused to one or more influenza peptides, such as M2e; see, e.g., WO 2005/055957), and *C. difficile* toxoid vaccines (including, e.g., toxoids A and/or B).

The compositions described above and elsewhere herein can be in a freeze-dried form, or in the form of a liquid, such as before or after a freeze-drying process. As is discussed in further detail elsewhere herein, the compositions of the invention are particularly advantageous because of the stability of the active components, which is due in large part to the formulation and the process by which the product is prepared, which involves lyophilization. In general, this process includes the following steps: freezing, primary drying, secondary drying, and stoppering. The process is described in further detail below, in the experimental examples, but an example of the process is as follows.

In the freezing step, the lyophilizer shelves are pre-cooled to −50° C. Once all trays are loaded, the shelves are held at −50° C. for 120 minutes. In the primary drying step, the vacuum is set to 25 mT, and the following ramp steps are carried out: ramp at +0.1° C./minute to a shelf temperature of −40° C., hold for 500 minutes; ramp at +0.1° C./minute to a shelf temperature of −35° C., hold for 500 minutes; ramp at +0.1° C./minute to a shelf temperature of −30° C., hold for 500 minutes, and ramp at +0.1° C./minute to a shelf temperature of −25° C., hold for 800 minutes. In the secondary drying step, the vacuum remains at 25 mT, and a ramp step is carried out such that ramping is at +0.1° C./minute to a shelf temperature of +20° C., hold for 800 minute. If necessary, the product can be held at +20° C., 25 mT up to 24 additional hours before stoppering. In the stoppering step, the chamber is outgassed with 0.22 µm filtered, dry, nitrogen gas, the vacuum is set to 800 mbar (slight vacuum), and stoppers are pushed into vials. An alternative lyophilization cycle that can be used in the invention is summarized in the following table.

TABLE 1

Alternative Lyophilization Cycle

| Step | Shelf Temperature | Hold Time |
|---|---|---|
| Freezing Cycle | | |
| Pre-cool lyophilizer shelves | 5° C. | Not applicable |
| Load trays, hold | 5° C. | >30 minutes |
| Ramp at −2.0° C./minutes | −5° C. | 15 minutes |
| Ramp at −1.0° C./minutes | −40° C. | 60 minutes |

TABLE 1-continued

Alternative Lyophilization Cycle

| Step | Shelf Temperature | Hold Time |
|---|---|---|
| Primary Drying | | |
| Set vacuum to 25 mT | | |
| Ramp at +0.5° C./minutes | +5° C. | 300 minutes |
| Ramp at −0.5° C./minutes | 0° C. | 300 minutes |
| Secondary Drying | | |
| Vacuum 25 mT | | |
| Ramp at +0.2° C./minutes | +30° C. | 600 minutes |
| Ramp at −1.0° C./minutes | +5° C. | 9999 minutes |
| Stoppering | | |
| Outgas the chamber with 0.22 µm filtered, dry, nitrogen gas | +20° C. | Not applicable |
| Set vacuum to 800 mbar (slight vacuum) | +20° C. | Not applicable |
| Push stoppers into vials | +20° C. | Not applicable |
| Outgas the chamber with 0.22 µm filtered, dry, nitrogen gas to atmospheric pressure | +20° C. | Not applicable |

Thus, the methods of the invention can involve freezing at or to about, for example, −70° C. to −30° C. (e.g., −60° C. to −40° C., or −50° C.). The freezing can be carried out for about 30 to 240 minutes (e.g., 60 to 120 minutes) or longer. The material can then be subject to one or more drying steps, as described herein. In these steps, a vacuum can be applied (e.g., 25 mT) and the temperature can be changed gradually (e.g., 0.1 to 1.0° C./minute, or 0.5° C./minute), over the course of a period of time (such as, 100-1000 minutes, e.g., 200-600 or 300-500 minutes). In the primary drying, the temperature may be raised to or about, for example, −30° C. to +10° C., e.g., −20° C. to +5° C. or −15° C. to 0° C., while in the secondary drying, the temperature may be changed to, for example, +5° C. to +35° C., e.g., 10° C. to 30° C., or 15° C. to 20° C. As is known by those of skill in this art, these parameters (e.g., temperatures, hold times, ramp rates, and vacuum levels) can be changed based on, for example, results obtained.

Prior to formulation, viruses (including chimeras) that may be included in the compositions of the invention can be made using standard methods in the art. For example, an RNA molecule corresponding to the genome of a virus can be introduced into primary cells, chick embryos, or diploid cell lines, from which (or the supernatants of which) progeny virus can then be purified. Another method that can be used to produce the viruses employs heteroploid cells, such as Vero cells (Yasumura et al., Nihon Rinsho 21:1201-1215, 1963). In this method, a nucleic acid molecule (e.g., an RNA molecule) corresponding to the genome of a virus is introduced into the heteroploid cells, virus is harvested from the medium in which the cells have been cultured, harvested virus is treated with a nuclease (e.g., an endonuclease that degrades both DNA and RNA, such as Benzonase™; U.S. Pat. No. 5,173,418), the nuclease-treated virus is concentrated (e.g., by use of ultrafiltration using a filter having a molecular weight cut-off of, e.g., 500 kDa), and the concentrated virus is formulated for the purposes of vaccination. Details of this method are provided in WO 03/060088 A2, which is incorporated herein by reference.

The vaccine compositions of the invention can be administered as primary prophylactic agents to those at risk of infection, or can be used as secondary agents for treating infected patients. Because the viruses in some of these compositions are attenuated, they are particularly well suited for administration to "at risk individuals" such as the elderly, children, or HIV infected persons. Such vaccines can also be used in veterinary contexts, e.g., in the vaccination of horses against West Nile virus infection, or in the vaccination of birds (e.g., valuable, endangered, or domestic birds, such as flamingos, bald eagles, and geese, respectively). Further, the vaccines of the invention can include a virus, such as a chimeric virus, including a particular mutation, in a mixture with viruses lacking such mutations.

The vaccines of the invention can be administered using methods that are well known in the art, and appropriate amounts of the vaccines to be administered can readily be determined by those of skill in the art. What is determined to be an appropriate amount of virus to administer can be determined by consideration of factors such as, e.g., the size and general health of the subject to whom the virus is to be administered. For example, the viruses of the invention can be formulated as sterile aqueous solutions containing between $10^2$ and $10^8$, e.g., $10^3$ to $10^7$, infectious units (e.g., plaque-forming units or tissue culture infectious doses) in a dose volume of 0.1 to 1.0 ml, to be administered by, for example, intramuscular, subcutaneous, or intradermal routes. In addition, because flaviviruses may be capable of infecting the human host via mucosal routes, such as the oral route (Gresikova et al., "Tick-borne Encephalitis," In The Arboviruses, Ecology and Epidemiology, Monath (ed.), CRC Press, Boca Raton, Fla., 1988, Volume IV, 177-203), flavivirus-based vaccines of the invention can be administered by mucosal routes as well. Further, the vaccines of the invention can be administered in a single dose or, optionally, administration can involve the use of a priming dose followed by a booster dose that is administered, e.g., 2-6 months later, as determined to be appropriate by those of skill in the art.

EXPERIMENTAL EXAMPLES

The experiments described below were carried out in a development program for the formulation and lyophilization of two vaccines, ChimeriVax™-WN (chimeric flavivirus including yellow fever virus capsid and non-structural proteins and West Nile virus pre-membrane/membrane and envelope proteins) and ChimeriVax™-JE (chimeric flavivirus including yellow fever virus capsid and non-structural proteins and Japanese Encephalitis virus pre-membrane/membrane and envelope proteins), but these approaches are included in the invention with respect to the formulation and processing of other protein/peptide and/or virus-containing therapeutic products as well, as is discussed above.

Thus, in one example, a formulation of the invention includes 10 mM histidine (amino acid), 50 mM potassium glutamate (amino acid), 0.1% HSA (Human Serum Albumin, USP), 5% mannitol, and 4% lactose, pH 7.9-8.1. In an example of the methods of the invention, lyophilization is carried out as follows. Lyophilizer shelves are pre-cooled to $-50°$ C., and once all of the trays are loaded, the shelves are held at $-50°$ C. for 120 minutes. In a primary during step, the vacuum is set to 25 mT, and the steps include: ramp at $+0.1°$ C./minute to a shelf temperature of $-40°$ C., hold for 500 minutes; ramp at $+0.1°$ C./minute to a shelf temperature of $-35°$ C., hold for 500 minutes; ramp at $+0.1°$ C./minute to a shelf temperature of $-30°$ C., hold for 500 minutes; and ramp at $+0.1°$ C./minute to a shelf temperature of $-25°$ C., hold for 800 minutes. In a secondary drying step, the vacuum remains at 25 mT, and ramp at $+0.1°$ C./minute to a shelf temperature of $+20°$ C., hold for 800 minutes. If necessary, the product can be held at $+20°$ C., 25 mT, up to 24 additional hours before stoppering. In a stoppering step, the chamber is outgassed with 0.22 µm filtered, dry, nitrogen gas, the vacuum is set to 800 mbar (slight vacuum), and stoppers are pushed into vials. The basis for this example, as well as other formulations and methods included in the invention is provided, in part, below.

Example 1

West Nile Lyophilization Study with Mannitol/Lactose Formulations (WNPD-045) Experiment In the experiment described in this example, we explored formulations of West Nile with a base of 5% mannitol, 4% lactose, and 10 mM histidine. Complete formulations are shown in Table 2, with the associated glass transition temperatures.

TABLE 2

WNPD-045 Formulations and Glass Transition Temperatures

| | Base | Additional Components | Tg |
|---|---|---|---|
| 1 | 5% Manntiol, 4% Lactose, 10 mM Histidine | 0.1% HSA, 50 mM K Glutamate | −42.4 |
| 2 | 5% Manntiol, 4% Lactose, 10 mM Histidine | 0.1% rHG-272, 50 mM K Glutamate | −42.1 |
| 3 | 5% Manntiol, 4% Lactose, 10 mM Histidine | 0.1% HSA | −40.1 |
| 4 | 5% Manntiol, 4% Lactose, 10 mM Histidine | 0.1% rHG-272 | −39.8 |

Virus was formulated by performing a 1:100 dilution of WNPD-001 Clarified Bulk into the formulation buffers. Formulation was done in a BSC. The lyophilization was carried out under the following conditions: ramp at 0.5° C./minute to a shelf temperature of $-55°$ C. and hold for 120 minutes; when product temperature reaches $-50°$ C., hold for 15 minutes; dry with chamber at 150 mT and foreline at 100 mT; ramp at 0.2° C./minute to a shelf temperature of $-20°$ C. and hold for 1034 minutes at 50 mT; and ramp at 0.53° C./minute to a shelf temperature of 20° C. at 50 mT and hold for roughly 862 minutes. This lyophilization cycle was completed in approximately 38 hours.

An accelerated stability study was performed on the lyophilized material. A number of lyophilized vials were incubated at 37° C. On days 7 and 14, vials were removed, labeled, and placed at $-80°$ C. for storage. All formulations with potassium glutamate had experienced considerable cake shrinkage after 7 days at 37° C. Formulations without potassium glutamate did not experience this shrinkage. Experiments WNPD-049 and WNPD-051 were PFU assays to determine the stability of the virus in these formulations. All samples were reconstituted with WFI.

Results

All formulations appeared very similar after lyophilization. The cakes were full and did not appear to suffer significant volume losses. Some cakes had detached from the vial walls, but this appeared to be random among the formulations. Table 3 shows the freezing yields and the yields across lyophilization compared to the Clarified Bulk material used in formulation. Table 4 shows the results of the accelerated stability study at 37° C.

TABLE 3

WNPD-045 Lyophilization and Freezing Yields

| WNPD-045 Stability at 37° C. | Assay | Frozen (−80° C.) Titer | Days at −80° C. | Freezing Yield | Titer Day 0 | Lyo Yield |
|---|---|---|---|---|---|---|
| WNPD-045, 5% Mannitol, 4% Lactose, 10 mM Histidine, 0.1% HSA, 50 mM Potassium Glutamate | WNPD-049 WNPD-051 | 1.67E+05 1.80E+05 | 7 14 | 103% 79% | 1.29E+05 1.55E+05 | 80% 68% |
| WNPD-045, 5% Mannitol, 4% Lactose, 10 mM Histidine, 0.1% rHG-272, 50 mM Potassium Glutamate | WNPD-049 WNPD-051 | 5.40E+04 5.80E+04 | 7 14 | 34% 26% | 7.80E+04 1.57E+05 | 48% 69% |
| WNPD-045, 5% Mannitol, 4% Lactose, 10 mM Histidine, 0.1% HSA | WNPD-049 WNPD-051 | 1.55E+05 1.46E+05 | 7 14 | 96% 64% | 1.45E+05 1.23E+05 | 90% 54% |
| WNPD-045, 5% Mannitol, 4% Lactose, 10 mM Histidine, 0.1% rHG-272 | WNPD-049 WNPD-051 | 2.18E+05 3.30E+04 | 7 14 | 135% 15% | 3.10E+04 7.90E+04 | 19% 35% |

TABLE 4

WNPD-045 Stability at 37° C.

| WNPD-045 Stability at 37° C. | Assay | Titer Day 0 | Titer Day 7 | Day 7 Log Loss | Titer Day 14 | Day 14 Log Loss |
|---|---|---|---|---|---|---|
| WNPD-045, 5% Mannitol, 4% Lactose, 10 mM Histidine, 0.1% HSA, 50 mM Potassium Glutamate | WNPD-049 WNPD-051 | 1.29E+05 1.55E+05 | 5.99E+04 8.21E+04 | 0.33 0.27 | 7.64E+04 | 0.31 |
| WNPD-045, 5% Mannitol, 4% Lactose, 10 mM Histidine, 0.1% rHG-272, 50 mM Potassium Glutamate | WNPD-049 WNPD-051 | 7.80E+04 1.57E+05 | 1.51E+04 1.05E+04 | 0.71 1.17 | 3.40E+03 | 1.66 |
| WNPD-045, 5% Mannitol, 4% Lactose, 10 mM Histidine, 0.1% HSA | WNPD-049 WNPD-051 | 1.45E+05 1.23E+05 | 6.39E+04 5.61E+04 | 0.36 0.34 | 3.83E+04 | 0.51 |
| WNPD-045, 5% Mannitol, 4% Lactose, 10 mM Histidine, 0.1% rHG-272 | WNPD-049 WNPD-051 | 3.10E+04 7.90E+04 | 4.50E+03 3.20E+03 | 0.84 1.39 | 3.70E+03 | 1.33 |

CONCLUSIONS

The formulations with HSA performed very well and had some of our best results to date. There were not significant losses in the −80° C. storage. These formulations also showed very good lyophilization yields with an average yield of 73%. It should be noted that the cake appearance of these samples was much more uniform than in any other formulation thus far. The stability of the HSA formulations is very encouraging. Both formulations showed <0.5 log loss after 14 days at 37° C. It appears that having potassium glutamate is beneficial to the formulation.

The formulations with recombinant human gelatin, rHG-272, did not produce results that were as good as those for HSA, but may improve if the 0.1% concentration is increased. These formulations showed low yields when frozen at −80° C. This supports data seen in WNPD-033 (see below), which had low recoveries after freezing in a rHG-272 formulation. The formulations with recombinant gelatin also showed losses (>1 log) in the stability studies at 37° C. after 14 days.

Example II

Development of a Lyophilized Vaccine for ChimeriVax™-WN and ChimeriVax™-JE Products This example describes the development and characterization of a formulation suitable for ChimeriVax™-WN and ChimeriVax™-JE vaccines, as well as the development and optimization of a lyophilization cycle for these vaccines.

Experimental Procedure and Results

Procedures

Formulation

To formulate bulks for lyophilization experiments, a 1:100 dilution of concentrated ChimeriVax™-WN or ChimeriVax™-JE was executed into the formulation buffer. The formulation buffer composition varied according to the experiment plan. Samples of the formulated Bulk are taken before lyophilization and stored at −80° C. as "pre-lyo" samples.

Lyophilization

For experiments up to WNPD-070 and up to JEPD-144, lyophilizations were performed using a FTS DuraStop MP system. Beginning with JEPD-145, a Kinetics LyoStar II system was used. Lyophilization parameters were varied according to the experimental plan. 3 mL vials were used for all experiments. Typically, a 0.5 mL fill volume was used, however, a 0.3 mL fill volume was experimented with and will be noted when applicable.

ChimeriVax™-WN Plaque Assay

A plaque assay was used to assess the viral recoveries of the lyophilization process and the stability studies. Lyophilized ChimeriVax™-WN samples were reconstituted with either water for injection (WFI) or 0.9% sodium chloride for injection. The reconstituted samples were diluted in WN PFU Media. Dilutions were plated 100 μl per well on O-Vero plates seeded at 2×10⁵ cells per well. Plates were incubated for 1 hour at 37° C. and 5% $CO_2$ and then overlayed with methyl cellulose overlay. Plates were incubated for 96±12 hours at 37° C. and 5% $CO_2$ and then stained with 1% crystal violet in 70% methanol. Stained plates are rinsed and then counted. Acceptable dilutions had between 10-120 plaques per well and have a relative standard deviation of <40% for all wells counted for each dilution.

ChimeriVax™-JE Plaque Assay

A plaque assay was used to assess the viral recoveries of the lyophilization process and the stability studies. Lyophilized ChimeriVax™-JE samples were reconstituted with either water for injection (WFI) or 0.9% sodium chloride for injection. The reconstituted samples were diluted in JE PFU Media. Dilutions were plated 100 μl per well on O-Vero plates seeded at 3×10⁵ cells per well. Plates were incubated for 1 hour at 37° C. and 5% $CO_2$ and then overlayed with methyl cellulose overlay. Plates were incubated for 96±12 hours at 37° C. and 5% $CO_2$ and then stained with 1% crystal violet in 70% methanol. Stained plates are rinsed and then counted. Acceptable dilutions had between 10-120 plaques per well and have a relative standard deviation of <40% for all wells counted for each dilution.

Stability Studies

Stability studies were conducted at a number of temperatures. Accelerated stability studies were done in a 37° C. incubator. Samples were also kept at ambient temperature (15-30° C.), 25° C., 2-8° C., and −20° C. Time zero samples were stored at −80° C. In some instances, samples were pulled from elevated temperatures on specific days and stored at −80° C. to be assayed at a later date.

Residual Moisture Analysis

Residual moisture analysis was performed using direct sample injection into a Coulometric Karl Fischer. The testing was done by Acambis' Quality Control group in Canton, Mass. according to US02-FRM-158-02.

Differential Scanning Calorimetry

Differential Scanning Calorimetry was performed using a TA Instruments Q1000. Liquid samples were cooled to −70° C. and then ramped to 20° C. When higher resolution was necessary, a modulated method was used. These methods produced glass transition temperatures for the formulation buffer candidates. Solid samples were ramped from 0° C. to 120° C. This method was used to evaluate the glass transition temperature of lyophilized material and to determine the storage conditions.

Results

Formulation Development Overview

Formulations were evaluated based on the following criteria:

Tg'—glass transition temperature of frozen material
Lyophilized cake appearance
Lyophilization recovery
Stability of lyophilized material at 37° C.
Residual moisture of lyophilized material
Tg—glass transition temperature of lyophilized material A large number of excipients were evaluated in early formulation experiments. Components initially screened include: sorbitol, mannitol, sucrose, dextran, lactose, glycine, Heatstarch, Pentastarch, PEG 3350, PVP 40K, sodium chloride, potassium chloride, Tween-80, histidine, alanine, HEPES, TRIS, potassium glutamate, tripolyphosphate, and potassium phosphate. Some formulations failed to produce acceptable cakes and had very low viral recoveries (less than 30%) after being lyophilized. Viral recoveries began to improve with the addition of HSA to formulations as a stabilizer.

HSA Experiments

In experiment WNPD-021, HSA was first used as a stabilizer. Different concentrations of HSA were added to two base formulations. The two formulations were:

1% Hetastarch, 1% sucrose, 0.1% sorbitol, and 50 mM potassium glutamate
4% lactose, 2% sorbitol, 10 mM histidine, 10 mM alanine, and 50 mM potassium glutamate and HSA was added at concentrations of 0%, 0.2%, 1%, and 2%.

A plaque assay showed the following yields upon reconstitution with WFI.

TABLE 5

| WNPD-021 Lyophilization Yields | |
|---|---|
| Formulation | Yield |
| WNPD-021 Hetastarch, 0.2% HSA | 40.10% |
| WNPD-021 Hetastarch, 2% HSA | 28.06% |
| WNPD-021 lactose/sorbitol, 0.2% HSA | 41.33% |
| WNPD-021 lactose/sorbitol, 2% HSA | 39.80% |

Experiment JEPD-018 further explored the effect of HSA as a stabilizer in lyophilized formulation. This experiment used the 4% lactose, 2% sorbitol, 10 mM histidine, 10 mM alanine, and 50 mM potassium glutamate formulation, and examined HSA concentrations of 0%, 0.05%, 0.1%, 1%, and 2%. After lyophilization, samples were stored at 37° C. in an accelerated stability study. Table 6 shows that the presence of HSA greatly improves the viral yield after lyophilization. Samples titered after 5, 12, and 19 days at 37° C. showed remarkably good recovery (FIG. 1). There does not seem to be any significant improvement with HSA concentrations higher than 0.1%, so it was decided to focus on formulations using 0.1% HSA.

TABLE 6

| JEPD-018 Lyophilization Yields and Accelerated Stability Data from 37° C. | | | | | | | | | |
|---|---|---|---|---|---|---|---|---|---|
| Formulation | pre-lyo | Day 0 | Lyo yield | 5 Days at 37 C. | Day 5 Log Loss | 12 Days at 37 C. | 12 Day Log Loss | 19 Days at 37 C. | 19 Day Log Loss |
| 2% HSA | 2.93E+04 | 2.31E+04 | 79% | 7.70E+03 | 0.48 | 6.19E+03 | 0.57 | | |
| 1% HSA | 2.35E+04 | 2.52E+04 | 107% | | | 9.41E+03 | 0.43 | 4.60E+03 | 0.74 |
| 0.2% HSA | 2.33E+04 | 2.62E+04 | 112% | 1.01E+04 | 0.41 | 9.98E+03 | 0.42 | 6.40E+03 | 0.61 |
| 0.1% HSA | 2.42E+04 | 2.06E+04 | 85% | 9.38E+03 | 0.34 | 8.70E+03 | 0.37 | | |
| 0.05% HSA | 2.06E+04 | 2.00E+04 | 97% | 3.15E+03 | 0.80 | 8.93E+03 | 0.35 | | |
| 0% HSA | 5.17E+03 | 1.30E+03 | 25% | 7.04E+02 | 0.27 | | | | |

Recombinant stabilizers were also evaluated to explore the possibility of eliminating HSA. Experiment JEPD-080 examined the use of Delta Biologics' Recombinant HSA and Fibrogen's recombinant Human Gelatin (2 strains—a wild type and an engineered). The recombinant Human Gelatin (rHG) products were used at concentrations of 0.5% and 1%. All stabilizers were used in a base formulation of 5% mannitol, 4% lactose, 10 mM histidine, and 50 mM potassium glutamate. The recombinant HSA performed comparable to the non-recombinant, however, the gelatin products generally had poor lyophilization recoveries and exhibited poor stability in studies at 37° C.

glutamate showed a better stability at 37° C. than that without. After 28 days, there was a 0.26 LOG loss in titer for the formulation with potassium glutamate. Without the potassium glutamate, there was a 0.56 log loss. Based on these data, it was decided to include 50 mM potassium glutamate in the formulation.

Selecting Bulking Agents

Lactose was first investigated as a formulation component in WNPD-021. This experiment produced encouraging lyo-

TABLE 7

JEDP-080 Lyophilization Yields and Accelerated Stability Data from 37° C.

| Formulation | −80° C. Yield | Lyo Yield | Yield after 9 days at 37° C. | Yield after 12 days at 37° C. | Log Loss after 12 days at 37° C. | Titer after 12 days at 37° C. |
|---|---|---|---|---|---|---|
| 0.2% HSA | — | 89% | 41% | 28% | 0.55 | 3.43E+05 |
| 0.2% recombinant HSA | 81% | 95% | 32% | 28% | 0.56 | 2.92E+05 |
| 0.5% Porcine Gelatin | 81% | 38% | 15% | 3% | 1.56 | 1.15E+04 |
| 1.0% Porcine Gelatin | 93% | 93% | 11% | 1% | 2.16 | 8.10E+03 |
| 0.5% rHG (engineered) | 88% | 101% | 3% | 2% | 1.64 | 2.82E+04 |
| 1.0% rHG (engineered) | 70% | 48% | 7% | 3% | 1.53 | 1.33E+04 |
| 0.5% rHG (wild type) | 74% | 41% | 14% | 5% | 1.30 | 2.08E+04 |
| 1.0% rHG (wild type) | 63% | 35% | 15% | 3% | 1.48 | 9.90E+03 |

Selecting Buffer Components

Histidine was chosen as a buffer component because it has a pK value near the optimal pH range for the ChimeriVax™ products. Our target pH range is 7.9-8.1 and histidine has a $pK_3'$ of 8.97. Experiment WNPD-033 tested a formulation of 5% sucrose, 0.1% HSA, and 50 mM potassium glutamate, with and without 10 mM histidine. These formulations were lyophilized and put on an accelerated stability study at 37° C. The two lyophilized formulations had very similar yields philization yields, shown in Table 5, and lactose was further investigated in JEPD-018 and showed very promising results in accelerated stability studies (Table 6 and FIG. 1).

Experiment WNPD-029 elaborated upon these encouraging results. This experiment used a base formulation of 4% lactose, 2% sorbitol, 10 mM histidine, 10 mM alanine, and 50 mM potassium glutamate. The data below reinforced the benefits of using HSA as a stabilizing component.

TABLE 8

WNPD-029 Lyophilization Yields and Accelerated Stability Data from 37° C.

| WNPD-029 Stability Study | Volume | Average PFU/mL | Total PFU | Step Yield | Log Loss |
|---|---|---|---|---|---|
| Clarified Bulk (from WNPD-029) | 0.1 | 4.83E+07 | 4.83E+06 | | |
| WNPD-029 lactose/sorbitol, Day 0 | 10 | 1.40E+04 | 1.40E+05 | 2.90% | 1.54 |
| WNPD-029 lactose/sorbitol, 7 Days at 37° C. | 10 | 1.90E+03 | 1.90E+04 | 13.57% | 0.87 |
| WNPD-029 lactose/sorbitol, 14 Days at 37° C. | 10 | 3.00E+02 | 3.00E+03 | 2.14% | 1.67 |
| WNPD-029 lactose/sorbitol, 0.1% HSA, Day 0 | 10 | 3.42E+05 | 3.42E+06 | 70.81% | 0.15 |
| WNPD-029 lactose/sorbitol, 0.1% HSA, 7 Days at 37° C. | 10 | 3.48E+05 | 3.48E+06 | 101.84% | −0.01 |
| WNPD-029 lactose/sorbitol, 0.1% HSA, 14 Days at 37° C. | 10 | 1.28E+05 | 1.28E+06 | 37.37% | 0.43 | upon reconstitution (74% without histidine, 87% with histidine), and showed similar stability profiles at 37° C. (FIG. 2). Despite similar profiles with and without histidine, it was selected as a formulation component because of its buffering capacity in the target pH range.

Experiment WNPD-045 examined formulations of 5% mannitol, 4% lactose, 0.1% HSA, and 10 mM histidine, with and without 50 mM potassium glutamate. These two formulations were lyophilized and then incubated at 37° C. for 28 days. Samples were taken at 7 day intervals during the 37° C. incubation to create the stability profile shown in FIG. 3. Both formulations had comparable yields after lyophilization (above 80%). The formulation with 50 mM potassium In Experiment JEPD-145, lactose concentration was varied. Concentrations of 2% lactose, 3% lactose, and 4% lactose were all lyophilized in combination with 5% mannitol, 0.1% HSA, 10 mM histidine, and 50 mM potassium glutamate. This experiment showed that 3% and 4% lactose behaved similarly, but 2% lactose was performed less well in the accelerated stability study (FIG. 4). Since there was no perceived advantage in using 3% lactose, studies were continued using 4% as the lactose concentration.

Experiment WNPD-036 compared the following three formulations:
 4% lactose, 2% sorbitol, 10 mM histidine, 10 mM alanine, 50 mM potassium glutamate, 0.1% HSA
 4% lactose, 3% sucrose, 10 mM histidine, 50 mM potassium glutamate, 0.1% HSA
 4% lactose, 3% mannitol, 10 mM histidine, 0.1% HAS

TABLE 9

WNPD-036 Lyophilization Yields and Accelerated Stability Data from 37° C.

| WNPD-036 Stability Study (from WNPD-042) | Average PFU/mL | Step Yield | Log Loss |
|---|---|---|---|
| WNPD-036 4% lactose, 2% sorbitol, pre-lyo | 2.65E+05 | | |
| WNPD-036 4% lactose, 2% sorbitol, Day 0 | 1.40E+05 | 52.93% | |
| WNPD-036 4% lactose, 2% sorbitol, 6 Days at 37° C. | 8.76E+04 | 62.57% | 0.20 |
| WNPD-036 4% lactose, 2% sorbitol, 14 Days at 37° C. | 5.31E+04 | 37.93% | 0.42 |
| WNPD-036 4% lactose, 3% sucrose, pre-lyo | 1.71E+05 | | |
| WNPD-036 4% lactose, 3% sucrose, Day 0 | 1.41E+05 | 82.16% | |
| WNPD-036 4% lactose, 3% sucrose, 6 Days at 37° C. | 5.10E+04 | 36.30% | 0.44 |
| WNPD-036 4% lactose, 3% sucrose, 14 Days at 37° C. | 1.42E+04 | 10.11% | 1.00 |
| WNPD-036 4% lactose, 3% mannitol, 10 mM histidine, pre-lyo | 1.59E+05 | | |
| WNPD-036 4% lactose, 3% mannitol, 10 mM histidine, Day 0 | 1.95E+05 | 122.64% | |
| WNPD-036 4% lactose, 3% mannitol, 10 mM histidine, 6 Days at 37° C. | 4.11E+04 | 21.08% | 0.68 |
| WNPD-036 4% lactose, 3% mannitol, 10 mM histidine, 14 Days at 37° C. | 1.39E+05 | 71.31% | 0.15 |

The lactose/mannitol formulation performed well. It had excellent recovery after lyophilization, and showed only 0.15 log loss in titer after two weeks at 37° C. This was selected as a candidate for further research. It was hoped that the crystallizing properties of mannitol could be used to speed up the lyophilization cycle.

Single Sugar Formulations

Other experiments explored using these bulking agents separately. WNPD-030 examined formulations containing only mannitol or sucrose. Lactose was investigated in WNPD-047. These formulations were compared to a formulation containing the two-sugar combination of 5% mannitol and 4% lactose from WNPD-045. The stability of the WNPD-045 formulation (5% mannitol, 4% lactose, 0.1% HSA, 10 mM histidine, 50 mM potassium glutamate) fax exceeded that of any of the single sugar formulations. All of the single sugar formulations showed viral titer losses greater than 0.9 log after 14 days at 37° C. The mannitol/lactose formulation only had 0.46 log loss in the same time period. This is illustrated in FIG. 5.

Annealing

Annealing was attempted in two lyophilization experiments, JEPD-166 and JEPD-172. In these experiments, the vials were frozen at −50° C. and then raised at 0.8° C./minute to −15° C. and held for 180 minutes to anneal. Next, the temperature was lowered at 0.8° C./minutes to −50° C. and held for an additional 120 minutes before starting the primary drying.

Both experiments produced excellent cakes. Annealing allowed the mannitol to crystallize, and the cake appearance was that of a typical crystalline mannitol cake. However, the annealed material exhibited poor stability compared to all experiments, which produced cakes without annealing. Annealed samples showed nearly 1.0 log loss after two weeks of storage at 37° C., while non-annealed samples typically experienced losses in the range of 0.3-0.5 log for the same time period (FIG. 6).

These data, coupled with the data from the single sugar systems, lead to the conclusion that crystalline mannitol is not beneficial to the stability of ChimeriVax™ products.

Differential Scanning Calorimetry confirmed that annealing essentially crystallized all the mannitol. FIG. 7 shows a thermalgram of a 4% lactose solution, which has a glass transition of −32.6° C. FIG. 8 shows that when 5% mannitol is added to the formulation, the glass transition temperature is depressed approximately 6° C. to −38° C. However, annealing enables the mannitol to crystallize and restores the glass transition temperature to the range seen in the lactose-only thermalgram. The disappearance of this glass transition depression confirms that the mannitol has entirely crystallized.

Another conclusion can be drawn from these data. Lactose always remains in the amorphous state when lyophilized. Mannitol, in a formulation by itself, will lyophilize as a crystalline material, however, when combined with other sugars, mannitol can be either crystalline or amorphous. Previous experiments have shown poor stability in the following cases:

Lactose alone (4%)—in which lactose is amorphous

Mannitol alone (5%)—in which mannitol is crystalline

Lactose (4%) and mannitol (5%) Annealed—in which mannitol is crystalline and lactose is amorphous Good stability has only been demonstrated in one of formulations involving these two components. When lactose (4%) and mannitol (5%) are lyophilized without any annealing step, both the lactose and the mannitol remains in the amorphous state. It is therefore either the amorphous mannitol or the amorphous mannitol/lactose combination that imparts superior stability to lyophilized ChimeriVax™. Amorphous lactose alone has proved ineffective, as has mannitol in any sort of crystalline state.

Supporting Data for Final Formulation

As outlined above, 5% mannitol, 4% lactose, 0.1% HSA, 10 mM histidine, and 50 mM potassium glutamate (pH 7.9-8.1) was selected as the formulation buffer for ChimeriVax™ vaccines. A number of experiments were done to characterize the formulation, and to create and optimize a lyophilization cycle.

Liquid Stability

Data from WNPD-052, JEPD-072, and JEPD-087 can be examined to show that this formulation provides excellent stability in a real-time −80° C. storage trial. No statistically significant titer losses due to storage can be observed in these experiments (FIG. 9). This formulation should provide adequate stability to the ChimeriVax™ products when stored at −80° C. before lyophilization.

Differential Scanning Calorimetry

Differential Scanning Calorimetry (DSC) was used to determine the glass transition temperature (Tg') of this formulation. The FIG. 10 shows a thermalgram from a WNPD-045 sample. This was analyzed using modulated DSC to improve resolution. FIG. 11 is a sample from JEPD-172 that showed sufficient resolution without using the modulated scanning. Both samples show a low glass transition temperature (by midpoint) in the range of −38-−40° C.

Moisture Analysis

A trend can be seen when comparing the amount of residual moisture to the stability of the vaccine at 37° C. after 2 weeks. FIG. 12 presents data collected from experiments JEPD-072, JEPD-087, JEPD-145, JEPD-147, and JEPD-151, and shows the loss in titer compared to the percentage of residual moisture.

Lyophilization Parameters

The experiments shown in the Table 10 detail the parameters used in lyophilizing the final formulation. It also captures the viral yields after lyophilization, the percent moisture of the lyophilized cake, the appearance of the lyophilized cake, and 37° C. accelerated stability data from 1 and 2 weeks, as well as the maximum time-point from 37° C. incubation.

cycle from this experiment served as the model for the technical specifications that were given to the contract manufacturer.

Technical Specifications

These technical specifications were based on JEPD-151, but hold times were extended to compensate for potential scale issues with a different lyophilizer. These specifications were transferred to Walter Reed Army Institute of Research for contract fill-finish of ChimeriVax™-WN and ChimeriVax™-JE Phase I/II material.

Freezing Cycle
    Pre-cool lyophilizer shelves to −50° C.
    Once all trays are loaded, hold shelves at −50° C. for 120 minutes.

TABLE 10

Lyophilization Parameters for Experiments with Final Formulation

| Run # | WNPD-045 | WNPD-052 | JEPD-072 | JEPD-087 | JEPD-145 | JEPD-147 | JEPD-151 | JEPD-153 | JEPD-166 | JEPD-172 | JEPD-174 |
|---|---|---|---|---|---|---|---|---|---|---|---|
| Freezing | | | | | | | | | | | |
| Ramp | 0.5 | 2.5 | 0.25 | 0.5 | 0.5 | pre-cooled | pre-cooled | pre-cooled | pre-cooled | pre-cooled | Pre-cooled |
| Temp | −55 | −55 | −50 | −50 | −50 | −50 | −50 | −50 | −50 | −50 | −50 |
| Hold Time | 120 | 60 | 30 | 60 | 30 | 180 | 180 | 180 | 2000 | 120 | 120 |
| Primary Drying | | | | | | | | | | | |
| Ramp | 0.2 | 0.2 | 0.1 | 0.2 | 0.05 | 0.05 | 0.1 | 0.1 | 0.1 | 0.1 | 0.1 |
| mT | 50 | 50 | 50 | 50 | 50 | 50 | 25 | 25 | 25 | 25 | 25 |
| Temp 1 | −20 | −12 | −20 | −20 | −20 | 20 | −35 | −25 | −20 | −20 | −40 |
| Hold | 1034 | 2100 | 1500 | 1625 | 1500 | 1300 | 300 | 1000 | 1250 | 1000 | 500 |
| Temp 2 | | | | | | | −30 | | | | −35 |
| Hold | | | | | | | 300 | | | | 500 |
| Temp 3 | | | | | | | −25 | | | | −30 |
| Hold | | | | | | | 300 | | | | 500 |
| Temp 4 | | | | | | | −20 | | | | −25 |
| Hold | | | | | | | 300 | | | | 800 |
| Temp 5 | | | | | | | | | | | −20 |
| Hold | | | | | | | | | | | 600 |
| Secondary Drying | | | | | | | | | | | |
| Ramp | 0.53 | 0.5 | 0.2 | 0.2 | 0.2 | | 0.2 | 0.2 | 0.2 | 0.2 | 0.2 |
| mT | 50 | 50 | 50 | 50 | 25 | | 25 | 25 | 25 | 25 | 25 |
| Temp | 20 | 20 | 20 | 20 | 20 | | 20 | 20 | 30 | 20 | 20 |
| Hold | 862 | 360 | 630 | 1000 | 1000 | | 2300 | 500 | 400 | 600 | 650 |
| Notes | | | | | | | | | Annealed at −15 for 180 min | Annealed at −15 for 180 min | |
| Results | | | | | | | | | | | |
| Moisture | | | 1.60% | 0.87% | 0.92% | 1.31% | 0.55% | | | | |
| Lyo Yield | 83% | 84% | 67% | 56% | 50% | 86% | 93% | 72% | 76% | 74% | 69% |
| Cake Appearance | slight separation from walls | separation from walls | separation from corners and walls | very seperated from walls | cake layering | cake layering | some shrinkage at corners | shrinkage at corners | excellent | excellent | some corner shrinkage |
| LOG Loss 7 days at 37 C. | 0.31 | 0.13 | 0.45 | | 0.48 | 0.26 | 0.16* | 0.18* | 0.57 | 0.65 | 0.24 |
| LOG Loss 14 days at 37 C. | 0.37 | 0.25* | 0.65 | 0.45 | 0.46 | 0.55 | 0.26* | 0.32 | 0.96 | 0.94 | 0.49* |
| Max days at 37 C. | 28 | 96 | 70 | 126 | 34 | 33 | 23 | 14 | 23 | 16 | 7 |
| LOG loss at Max Day | 0.26 | 1.48 | 0.92 | 1.45 | 0.55 | 1.14 | 0.49 | 0.32 | 1.12 | 0.94 | 0.24 |

*denotes numbers are extrapolated from the stability curves

Based on these data, it was necessary to establish a lyophilization cycle that could be transferred to the contract manufacturer. JEPD-151 had the highest yield after lyophilization, the best stability after 2 weeks at 37° C., the lowest residual moisture, and produced some of the best cakes from an aesthetic standpoint (FIG. 13). The lyophilization Primary Drying
    Set vacuum to 25 mT.
    Ramp at +0.1° C./minute to a shelf temperature of −40° C., hold for 500 minutes.
    Ramp at +0.1° C./minute to a shelf temperature of −35° C., hold for 500 minutes.

Ramp at +0.1° C./minute to a shelf temperature of −30° C., hold for 500 minutes.
Ramp at +0.1° C./minute to a shelf temperature of −25° C., hold for 800 minutes.

Secondary Drying
Vacuum remains at 25 mT
Ramp at +0.1° C./minute to a shelf temperature of +20° C., hold for 800 minutes.
If necessary, the product can be held at +20° C., 25 mT up to 24 additional hours before stoppering.

Stoppering
Outgas the chamber with 0.22 μm filtered, dry, nitrogen gas.
Set vacuum to 800 mbar (slight vacuum).
Push stoppers into vials.

Materials and Equipment
Materials
 WN PFU Media—M199 Media (Gibco, Catalog #12340-030) containing 10% FBS (Hyclone, Catalog #SH30070.03) and 1× Penicillin/Streptomycin (Sigma, P4333)
 JE PFU Media—EMEM Media containing 10% FBS (Hyclone, Catalog #SH30070.03) and 1× Penicillin/Streptomycin (Sigma, P4333), 1×L-Glutamine (2 mM) (Gibco, Catalog #25030-018), and 20 mM HEPES
 Methyl Cellulose Overlay—Methyl Cellulose (prepared as per SOP#502-066) containing 5% or 10% FBS (Hyclone, Catalog #SH30070.03), 1×L-glutamine (Gibco, Catalog #25030-018), 1× Antibiotic/Antimycotic (Gibco, Catalog #15240-062)

Equipment
 FTS Durastop MP Lyophilizer
 Kinetics Lyostar II Lyophilizer
 Orion Karl Fischer Coulometric Titrator model AF7LC
 TA Instruments DSC Q1000 (ID#8769)
 Heraeus Heracell 240 Incubator (ID#9055)
 VWR Low Temperature Incubator Model 2005 (ID#s 8618 and 8617)
 VWR Refrigerator (ID#8663)
 Fischer Scientific Isotemp (ID#9059)
 Revco Ultima II (ID#9061)

CONCLUSIONS/DISCUSSION

The data presented in this example outline the selection and development of a formulation intended for the lyophilization of ChimeriVax™ products. The formulation has been thoroughly characterized, and has shown adequate stability in liquid form, and excellent recovery and stability after lyophilization. Prior to lyophilization, the formulated vaccine can be stored in liquid form at −80° C. without any significant affect on titer. This example also captures the development and optimization of a lyophilization cycle for a 0.5 mL fill in a 3 mL vial. This cycle should produce cakes of acceptable appearance, high recovery of virus (>70%), and low residual moisture (<2%). The lyophilized product has demonstrated excellent stability at elevated temperature, and will likely show no significant titer loss when stored at the storage conditions of ≤−10° C.

The contents of all publications noted above are incorporated herein by reference. Other embodiments are within the scope of the following claims.

What is claimed is:

1. A freeze-dried composition comprising a live, attenuated flavivirus, one or more stabilizers, one or more buffer components, lactose, and amorphous mannitol.

2. The composition of claim 1, wherein the stabilizer is human serum albumin (HSA).

3. The composition of claim 2, wherein the human serum albumin is non-recombinant human serum albumin (HSA) or recombinant human serum albumin (rHA).

4. The composition of claim 1, comprising histidine and/or potassium glutamate as a buffer component.

5. The composition of claim 2, wherein said human serum albumin is present in said composition at a concentration of about 0.05-2.0% prior to freeze-drying.

6. The composition of claim 1, wherein said mannitol and/or lactose is present in said composition at a concentration of about 2-10% prior to freeze-drying.

7. The composition of claim 4, wherein said histidine is present in said composition at a concentration of about 1-20 mM prior to freeze-drying.

8. The composition of claim 4, wherein said potassium glutamate is present in said composition at a concentration of about 20-80 mM prior to freeze-drying.

9. The composition of claim 1, wherein said live, attenuated flavivirus is a chimeric flavivirus that comprises a first flavivirus in which one or more structural proteins have been replaced with corresponding structural proteins of a second, different flavivirus.

10. The composition of claim 9, wherein the membrane and envelope proteins of said first flavivirus have been replaced with membrane and envelope proteins of said second, different flavivirus.

11. The composition of claim 10, wherein said first and second flaviviruses are, independently, selected from the group consisting of Yellow Fever, Japanese encephalitis, dengue-1, dengue-2, dengue-3, dengue-4, Murray Valley encephalitis, St. Louis encephalitis, West Nile, Kunjin, Rocio encephalitis, Ilheus, Central European encephalitis, Siberian encephalitis, Russian Spring-Summer encephalitis, Kyasanur Forest Disease, Alkhurma, Omsk Hemorrhagic fever, Louping ill, Powassan, Negishi, Absettarov, Hansalova, Apoi, and Hypr viruses.

12. The composition of claim 10, wherein said second flavivirus is a Japanese encephalitis virus, a West Nile virus, or a dengue virus, and said first flavivirus is a yellow fever virus.

13. The composition of claim 1, wherein the pH of said composition is 7.9-8.1 prior to freeze-drying.

14. The composition of claim 1, wherein said lactose is present at a concentration of about 2-10% and said mannitol is present at a concentration of about 2-10% prior to freeze-drying.

15. The composition of claim 14, wherein said lactose is present at a concentration of about 4% and said mannitol is present at a concentration of 5% prior to lyophilization.

16. The composition of claim 1, wherein said composition does not comprise alanine.

17. A liquid composition comprising a live, attenuated flavivirus, one or more stabilizers, one or more buffer components, lactose, and mannitol, wherein said mannitol is in amorphous form upon freeze-drying of said composition, and said live, attenuated flavivirus is a chimeric flavivirus that comprises a first flavivirus in which one or more structural proteins have been replaced with corresponding structural proteins of a second, different flavivirus.

18. The composition of claim 17, wherein the membrane and envelope proteins of said first flavivirus have been replaced with membrane and envelope proteins of said second, different flavivirus.

19. The composition of claim 18, wherein said first and second flaviviruses are, independently, selected from the group consisting of Yellow Fever, Japanese encephalitis, dengue-1, dengue-2, dengue-3, dengue-4, Murray Valley encephalitis, St. Louis encephalitis, West Nile, Kunjin, Rocio encephalitis, Ilheus, Central European encephalitis, Siberian encephalitis, Russian Spring-Summer encephalitis, Kyasanur Forest Disease, Alkhurma, Omsk Hemorrhagic fever, Louping ill, Powassan, Negishi, Absettarov, Hansalova, Apoi, and Hypr viruses.

20. The composition of claim 18, wherein said second *flavivirus* is a Japanese encephalitis virus, a West Nile virus, or a dengue virus, and said first *flavivirus* is a yellow fever virus.

* * * * *